US011623996B2

(12) United States Patent
Bonderer et al.

(10) Patent No.: US 11,623,996 B2
(45) Date of Patent: Apr. 11, 2023

(54) PROCESS AND MATERIAL FOR PRODUCING 3D OBJECTS BY ENERGY-PULSE-INDUCED TRANSFER PRINTING

(71) Applicants: Ivoclar Vivadent AG, Schaan (LI); IO Tech Group Ltd, London (GB)

(72) Inventors: Lorenz Josef Bonderer, Sargans (CH); Jürgen Lauberscheimer, Buchs (CH); Wolfgang Wachter, Schaan (LI); Michael Zenou, Hasmonaim (IL)

(73) Assignees: Ivoclar Vivadent AG, Schaan (LI); IO Tech Group Ltd., London (GB)

( * ) Notice: Subject to any disclaimer, the term of this patent is extended or adjusted under 35 U.S.C. 154(b) by 525 days.

(21) Appl. No.: 16/658,870

(22) Filed: Oct. 21, 2019

(65) Prior Publication Data
US 2020/0172747 A1  Jun. 4, 2020

(30) Foreign Application Priority Data

Nov. 29, 2018 (EP) .................................... 18209277

(51) Int. Cl.
| | | |
|---|---|---|
| *C09D 11/101* | (2014.01) | |
| *B29C 64/135* | (2017.01) | |
| *C09D 11/107* | (2014.01) | |
| *B33Y 70/00* | (2020.01) | |
| *C09D 11/38* | (2014.01) | |
| *A61K 6/30* | (2020.01) | |
| *A61K 6/887* | (2020.01) | |
| *C08K 3/16* | (2006.01) | |
| *C08K 3/36* | (2006.01) | |
| *A61K 6/62* | (2020.01) | |
| *B33Y 10/00* | (2015.01) | |
| *A61C 7/00* | (2006.01) | |
| *A61C 13/08* | (2006.01) | |
| *B29K 33/04* | (2006.01) | |

(52) U.S. Cl.
CPC .............. *C09D 11/101* (2013.01); *A61K 6/30* (2020.01); *A61K 6/62* (2020.01); *A61K 6/887* (2020.01); *B29C 64/135* (2017.08); *B33Y 70/00* (2014.12); *C08K 3/16* (2013.01); *C08K 3/36* (2013.01); *C09D 11/107* (2013.01); *C09D 11/38* (2013.01); *A61C 7/00* (2013.01); *A61C 13/08* (2013.01); *B29K 2033/04* (2013.01); *B33Y 10/00* (2014.12)

(58) Field of Classification Search
None
See application file for complete search history.

(56) References Cited

U.S. PATENT DOCUMENTS

| | | | |
|---|---|---|---|
| 5,877,232 A | 3/1999 | Storch et al. | |
| 6,043,361 A | 3/2000 | Evans et al. | |
| 6,096,903 A | 8/2000 | Moszner et al. | |
| 6,344,556 B1 | 2/2002 | Evans et al. | |
| 6,479,592 B2 | 11/2002 | Rheinberger et al. | |
| 6,569,917 B1 | 5/2003 | Moszner et al. | |
| 6,908,953 B2 | 6/2005 | Weinmann et al. | |
| 7,137,697 B2 | 11/2006 | Lehmann et al. | |
| 7,585,901 B2 * | 9/2009 | Moszner ............... | C07C 69/716 526/309 |
| 9,387,056 B2 | 7/2016 | Wachter et al. | |
| 9,532,930 B2 | 1/2017 | Burtscher et al. | |
| 2007/0232719 A1 * | 10/2007 | Moszner ............... | C07C 271/28 549/13 |
| 2015/0080490 A1 * | 3/2015 | Burtscher ............... | A61K 6/889 522/18 |
| 2015/0111176 A1 * | 4/2015 | Wachter ............... | B29C 64/135 430/269 |
| 2020/0171700 A1 | 6/2020 | Bonderer et al. | |
| 2020/0172444 A1 | 6/2020 | Bonderer et al. | |
| 2020/0172747 A1 * | 6/2020 | Bonderer ............. | C09D 11/107 |

FOREIGN PATENT DOCUMENTS

| | | |
|---|---|---|
| CA | 2207351 A1 | 12/1997 |
| CA | 2296227 A1 | 7/2000 |
| EP | 3335687 A1 | 6/2018 |

OTHER PUBLICATIONS

Database WPI Week 200838; Thomson Scientific, London, GB; AN 2008-F96087-&JP 2008 094732 A (Tokuyama Dental KK) Apr. 24, 2008 (Apr. 24, 2008). XP-002791806.

\* cited by examiner

*Primary Examiner* — Peter A Salamon
(74) *Attorney, Agent, or Firm* — Ann M. Knab; Thad McMurray

(57) ABSTRACT

The invention relates to a material for use as construction material for energy-pulse-induced transfer printing, which contains (a) at least one polymerizable binder, (b) at least one volume expansion component, (c) at least one initiator for the polymerization and (d) preferably at least one energy transformation component. The invention furthermore relates to a process for producing three-dimensional objects using the material.

23 Claims, No Drawings

PROCESS AND MATERIAL FOR PRODUCING 3D OBJECTS BY ENERGY-PULSE-INDUCED TRANSFER PRINTING

CROSS-REFERENCE TO RELATED APPLICATIONS

This application claims priority to European Patent Application No. 18209277.5 filed on Nov. 29, 2018, the disclosure of which is incorporated herein by reference in its entirety.

TECHNICAL FIELD

The invention relates to processes and materials which are suitable for producing three-dimensional objects by energy-pulse-induced transfer printing. The materials and processes are particularly suitable for producing dental restorations.

BACKGROUND

The term Additive Manufacturing (AM) combines additive manufacturing processes in which three-dimensional models or components are produced from computer-aided design data (CAD data). Known AM processes are e.g. stereolithography (SL), selective laser sintering (SLS), 3D printing, fused deposition modelling (FDM), inkjet printing (IJP), 3D plotting, multi-jet modelling (MJM), solid freeform fabrication (SFF), laminated object manufacturing (LOM), laser powder forming (LPF) and direct ceramic jet printing (DCJP). With these processes, models, components and shaped parts can be produced cost-effectively even in small batches.

EP 1 268 211 B1 and correspondng U.S. Pat. No. 7,137,697, which is hereby incorporated by reference, discloses a printing process in which a volumetric or positional change is induced by a focused laser beam locally in the material to be printed, with the result that an ink droplet detaches from the substantially homogeneous ink layer and is transferred onto the printing substrate. This process is called a laser induced forward transfer (LIFT) process. The material to be printed is transferred from the so-called donor or carrier substrate onto the receiver substrate (acceptor). The carrier substrate consists of a carrier which is coated with a thin layer of the material to be printed. This material layer is irradiated in a punctiform manner with a laser and thereby softened or melted and partially evaporated. In the case of transparent carriers the laser can be focused from the back through the carrier onto the material to be printed. If the carrier is not transparent, the carrier is heated by the laser and the material is indirectly softened or melted. Alternatively, the laser can be directed onto the material directly from above. The receiver substrate (printing substrate) is arranged at a small distance from the carrier substrate, which is to be maintained precisely. A part of the material to be printed is evaporated abruptly by the laser energy. The vapour cloud forming entrains a small quantity of the softened or melted material and deposits it on the receiver substrate.

In order to evaporate the material to be printed, the laser light must be absorbed and converted into heat. In the case of printing inks, the laser beam is usually absorbed by colour pigments which are contained in the inks. Alternatively, an absorption layer can be provided, which absorbs the laser light and then transfers the energy to the material to be printed. Such an absorption layer is usually arranged between the carrier and the material to be printed. Absorption layers are disadvantageous because parts of this layer are often transferred onto the receiver substrate together with the printing ink.

Zenou et al., small 2015, 11, No. 33, 4082-4089 describe the production of three-dimensional metal objects using the LIFT process. For this, they use metal-coated glass plates as carrier substrate. The metal is melted by a laser and transferred dropwise onto the receiver substrate. Three-dimensional metal structures are obtained by printing many layers one over another.

In 3D printing by means of stereolithography, the printable materials have to be flowable and photoreactive during processing. In 3D inkjet printing, the viscosity of the inks is significantly below 1 Pa·s and usually below 0.1 Pa·s. The viscosity requirements exclude higher-viscosity materials and suspensions with a high filler content. On the other hand, materials with high viscosity and a high filler content are preferred because a high viscosity of the starting substances and a high filler loading have a positive effect on the physical properties of the workpieces and make it possible to produce objects with high toughness, high breaking strength, good abrasion resistance and a high elastic modulus.

SUMMARY

The object of the invention is to provide an additive process for producing three-dimensional objects, by which high-viscosity materials can also be processed. In addition, different materials should be processed together to form an object. Moreover, materials are to be provided which are suitable for processing using this process and in particular for producing dental restorations.

DETAILED DESCRIPTION

This object is achieved by an additive process for producing three-dimensional objects, which preferably comprises the following steps:

(1) laminar application of a support/construction material to a carrier in a defined layer thickness, preferably in a layer thickness of 3-300 µm, particularly preferably 10-100 µm, (2) transfer of a portion of the support/construction material from the carrier substrate (donor) onto a receiver substrate (acceptor) by the local, site-selective input of an energy pulse, preferably a laser pulse, (3) solidification of the support/construction material on the receiver substrate, preferably by drying, radiation curing or altering the aggregation state (e.g. by temperature change), (4) repetition of steps (1)-(3) until the desired object has been constructed, (5) optionally removal of the support material and optional cleaning of the object, (6) optional post-tempering of the object by further curing, preferably by drying, radiation, heat or a combination thereof, (7) optional mechanical processing of the object, e.g. by vibratory finishing or manual processing such as grinding or polishing.

The curing of the layer in step (3) need not be carried out directly after application of the individual layer. It is also possible first to apply several layers one after another (step 2) and then to cure these layers together. The overall thickness of the layers to be cured together should preferably be 30 to 200 μm. Steps (2) and optionally (1) are therefore preferably repeated until the overall thickness lies in this range.

In step (1) the support/construction material is applied to a carrier and in step (2) is transferred from the carrier onto the receiver substrate. A carrier coated with support/construction material in step (1) can be used several times for the transfer of support/construction material onto the receiver substrate, for example by choosing an area of the coated carrier that has not yet been used. Step (2) can therefore be repeated several times without it being necessary to repeat step (1).

Steps (1) to (3) are repeated until the desired object is completed. According to a preferred embodiment the support/construction material is smoothed following step (3), preferably with a roller, blade, burr and/or a wiper.

As oxygen from the air can inhibit the polymerization at the surface of the component, a curing of the materials by polymerization is preferably carried out with exclusion of air (oxygen). The process can be carried out under protective gas, for example under a bell jar which is flushed with protective gas. Inert gases such as e.g. $N_2$, $CO_2$ or noble gases such as e.g. He or Ar are suitable as protective gas. According to a preferred embodiment an oxygen-poor atmosphere is generated by the evaporation of the volume expansion component in the region above the component which likewise counteracts an inhibition.

Once the object has been completed, it is preferably subjected to a further curing in an additional step (6) in order to cure residual monomers which remain in the case of curing in layers. For this, the body is heated e.g. to approx. 60° C. in dependence on the chosen initiator or preferably irradiated with light e.g. for 1 to 12 minutes.

The process is characterized in that a radically polymerizable material is used as construction material, preferably a material which contains
(a) at least one polymerizable binder, preferably a radically polymerizable binder,
(b) at least one volume expansion component,
(c) at least one initiator for the polymerization, preferably an initiator for the radical polymerization, particularly preferably a photoinitiator, and
(d) preferably at least one energy transformation component.

One or more different construction materials can be used in the process.

The construction material or construction materials can be processed together with a support material. By support materials is meant materials which are removed from the finished object. Construction materials, in contrast, are materials which form the object and which remain after the removal of the support material. The term "support/construction material" is to be understood as meaning that either a support material or a construction material is printed or that both materials are used together. Support and construction materials together are also called printing materials herein. The support material is optionally removed from the finished object in step (5).

Preferred carriers in step (1) are polymer films, preferably with a thickness of 10-200 μm, in particular PET, polyimide and polyvinyl chloride (PVC) films; glass carriers, preferably made of float glass or borosilicate glass; carriers made of non-metallic, inorganic, porous or non-porous materials; metallic carriers, preferably made of stainless steel, aluminium, titanium alloys, copper alloys such as bronze or brass; carriers made of non-metallic, inorganic materials such as ceramic carriers, preferably made of $ZrO_2$, $Al_2O_3$, zirconia-toughened alumina (ZTA), alumina-toughened zirconia (ATZ), $SiC_x$, $SiN_x$, diamond-like carbon, glassy carbon, BN, $B_4C$ or AlN; or carriers made of a combination of these materials. The carriers are chosen such that they behave sufficiently inertly vis-à-vis the support/construction material, i.e. in particular are not perceptibly swollen or corroded by the support or construction material within the application time.

The carrier can be present as a plate, single-use tape, endless tape, cylinder or hollow cylinder. The work surface can be flat or curved. Curved surfaces are preferably curved about an axis, like e.g. the lateral surface of a cylinder. The coated carrier is also called carrier substrate herein.

In order to support the formation of a homogeneous layer of the support or construction material, support/construction material and carrier are preferably matched to each other. A low interfacial tension between support/construction material and carrier is sought. For hydrophilic support/construction materials, hydrophilic carrier and/or receiver substrates are preferably used, for example glass carriers, cellophane or hydrophilic PET films.

Surfaces can be hydrophilized e.g. by flame, plasma or etching treatments. In general the printing material, i.e. support and/or construction material, is to wet the carrier well. The wetting can likewise be improved by the addition of a surfactant to the printing material. In the case of hydrophobic support/construction materials, hydrophobic carriers are preferred.

The support/construction material can be applied to the carrier in a known manner, preferably by scraper or doctor-blade systems, with slot nozzles (with or without dispenser), by flexographic or gravure printing, screen printing, pad printing, spray coating or by a combination of these processes. In general all the printing methods known in the state of the art are suitable for this. The coated carrier is also called carrier substrate herein.

In the case of printing cylinders the support/construction material is preferably deposited continuously onto a rotating cylinder. Through the rotation the layer of the material formed on the cylinder is transported in the direction of the energy source, e.g. the laser, and printed there. The printed material is then added to again during further rotation.

Carrier films can likewise be used in continuous processes, for example by forming them as a circulating tape. However, the coated films can also be ready-made for single use.

In step (2) a part of the energy introduced is absorbed by the support/construction material and converted into heat. The absorption preferably takes place in the support/construction material itself without an additional absorption layer on the carrier substrate, with the result that the disadvantages associated with such absorption layers are avoided.

The energy absorption brings about a local, abrupt volume expansion, for example an evaporation, of the volume expansion component in the material and leads to the detachment of the support/construction material from the carrier substrate and to the transfer onto the receiver substrate. Droplets of the support/construction material are transferred onto the receiver substrate, where they can coalesce and form, for example, a homogeneous film.

The energy input in step (2) is preferably effected via the side of the carrier substrate facing away from the support/construction material.

The receiver substrate can have a flat surface and should be at least large enough to accommodate the whole of the component to be printed. The receiver substrate preferably has a smooth surface, which can be closed or porous. By a porous surface is meant a surface which has pores with an average size of preferably 1 nm-10 µm. The pore size is determined using scanning electron microscopy by counting. The average values obtained in the process are specified.

Examples of materials with micro- or nanoporous surface are set, dry gypsum, partially sintered but still porous $ZrO_2$, nanoporous glass or microporous plastics, such as e.g. high-density polyethylene sintered together.

The use of porous receiver substrates can promote the drying of the support and construction materials, particularly those construction materials that contain solid particles, such as slips for the production of ceramic objects. Particularly when the solidification takes place through drying, a separate drying step can be omitted. However, it is to be ensured that the pores are smaller than the solid filler particles, so that they do not clog the pores during the drying.

According to the invention receiver substrates with a non-porous, i.e. closed, surface are preferably used.

The desired three-dimensional objects are produced by repeated layered printing of support and construction material. The individual layers can in each case be formed by the support material alone, by the construction material alone or by both materials together.

Support and construction materials can be printed together in one work step or one after another. For example, in a first work step a support material can be printed and then the construction material can be printed in or on the solidified support structure in the described manner. The deposited layer thicknesses of the support material and of the construction material can be different. It can thereby become necessary, e.g., for the number of deposited layers to be different for support material and for construction material. According to a preferred embodiment several layers of at least one support material are first deposited on the receiver substrate.

Then the desired object is formed by printing at least one construction material. Once the actual component has been completed, further layers of the support material can be applied, with the result that the top and bottom side of the printed object are delimited by one or more layers of the support material. In a particularly preferred embodiment the outer edge around the construction object in each layer is formed by the support material, with the result that the printed object is surrounded on all sides by support material. Thicker layers can be used in areas of the component in which the cross section does not change greatly, while thinner layers are preferred at points in which the component cross section changes rapidly.

In preparation for the next depositing cycle, the applied material layer can optionally be smoothed in a further process step, for example with a metal roller, a blade, a wiper or a burr with/without material suction.

The layered application is continued until the desired three-dimensional object is completed. The printing process is controlled by a computer by means of CAD data, as is usual in additive manufacturing processes. Construction material is used in the areas which form the shaped part and the support material is used underneath overhangs, on the sides of the component and in cavities.

In a preferred embodiment of the process the printing material, i.e. support or construction material, is applied to the carrier during the printing process. Alternatively, substrates already coated in advance can also be used, preferably in the form of coated carrier films. New printing material for the LIFT process is preferably provided by renewed, selective or continuous coating of the carrier substrate. Alternatively, substrates already coated in advance can also be used, preferably in the form of coated carrier films.

If a support material is used, it must be removed from the shaped body residue-free after the curing of the workpiece without damaging the shaped body (step 5), for example by dissolving in a suitable solvent and/or by melting. Moreover the support material can be removed by machine, e.g. by vibratory finishing, or manually, by ultrasonic cleaning or by spraying/washing off. Combinations of the named measures likewise come into consideration. For example, the support material can be softened by soaking in a solvent and then mechanically removed by machine or manually. In a particularly preferred embodiment the support material is melted and adhering support material residues are then removed using a solvent bath. The object is cleaned at the same time through the described measures.

For the post-curing (step 6) the component can be post-cured before, during or preferably after cleaning by irradiation with a radiation source, e.g. a mercury vapour lamp or LED lamp. This process can be supported by heating the component up to a maximum of 120° C.

The process according to the invention is preferably a LIFT process. By a LIFT process is meant here a process in which, as explained at the beginning, a small quantity of material is extracted from a printing material by an energy pulse and transferred onto a receiver substrate. The energy pulse is preferably generated by a laser. The laser beam is focused onto a small area of the support or construction material and the support or construction material is hereby heated locally so strongly that the volume expansion component expands abruptly, e.g. due to evaporation of a portion of the printing material. The energy transformation component absorbs the laser energy and transfers this to the volume expansion component. The abruptly evaporating volume expansion component entrains the support or construction material and transfers it onto the receiver substrate. It is also possible for the volume expansion component to absorb a part of the energy directly.

According to the invention, instead of a laser beam, another suitable energy source can be used, for example focused light (not laser) or particle beams such as electron or ion beams. For the sake of simplicity the term LIFT process is also used here for processes in which no laser is used. Lasers are preferred, in particular lasers with a wavelength of from 300 nm to 4000 nm, for example neodymium:YAG lasers with a wavelength of 1064 nm. Pulsed laser light with a pulse energy in the µJ range and a pulse duration of from 1 ns to 1 ps is particularly preferred.

The process according to the invention is characterized in that a material which preferably contains a radically polymerizable binder as binder (a) is used as construction material.

Mono- or multifunctional (meth)acrylates or mixtures thereof are particularly suitable as radically polymerizable binders. By monofunctional (meth)acryl compounds is meant compounds with one, by multifunctional (meth)acryl compounds is meant compounds with two or more, preferably 2 to 3, polymerizable groups. Suitable examples are methyl, ethyl, 2-hydroxyethyl, butyl, benzyl, tetrahydrofurfuryl or isobornyl (meth)acrylate; p-cumylphenoxyethylene glycol methacrylate (CMP-1E); bisphenol A di(meth)acrylate; bis-GMA (an addition product of methacrylic acid and bisphenol A diglycidyl ether); ethoxylated or propoxylated bisphenol A dimethacrylate, such as e.g. the bisphenol A dimethacrylate with 3 ethoxy groups (SR-348c, from Sartomer); or 2,2-bis[4-(2-methacryloxypropoxy)phenyl]propane; UDMA (an addition product of 2-hydroxyethyl methacrylate and 2,2,4-trimethylhexamethylene diisocyanate); di-, tri- or tetraethylene glycol di(meth)acrylate; trimethylolpropane tri(meth)acrylate; pentaerythritol tetra(meth)acrylate; as well as glycerol di- and trimethacrylate; 1,4-butanediol di(meth)acrylate; 1,10-decanediol di(meth)acrylate (D3MA); or 1,12-dodecanediol di(meth)acrylate. Preferred (meth)acrylate monomers are benzyl, tetrahydrofurfuryl or isobornyl methacrylate, p-cumyl-phenoxyethylene glycol methacrylate, 2,2-bis[4-(2-methacryloxypropoxy)phenyl] propane, bis-GMA, UDMA, SR-348c and D3MA.

N-mono- or N-disubstituted acrylamides such as e.g. N-ethylacrylamide or N,N-dimethacrylamide or bisacrylamides such as e.g. N,N'-diethyl-1,3-bis(acrylamido)propane, 1,3-bis(methacrylamido)propane, 1,4-bis(acrylamido)butane or 1,4-bis(acryloyl)piperazine can also be used as radically polymerizable binder.

Furthermore, known low-shrinkage radically ring-opening polymerizable monomers, such as e.g. mono- or multifunctional vinylcyclopropanes or bicyclic cyclopropane derivatives (cf. DE 196 16 183 C2 or EP 1 413 569 A1 and corresponding U.S. Pat. Nos. 7,365,222 and 7,585,901, which US patents are hereby incorporated by reference), or cyclic allylsulphides (cf. U.S. Pat. No. 6,043,361 or U.S. Pat. No. 6,344,556, which US patents are hereby incorporated by reference) which in addition can also be used in combination with the previously listed di(meth)acrylate crosslinkers can also be used as radically polymerizable binder.

Moreover, radically polymerizable polysiloxanes which can be produced from suitable methacryl silanes such as e.g. 3-(methacryloyloxy)propyltrimethoxysilane and are described e.g. in DE 199 03 177 C2 and corresponding U.S. Pat. No. 6,569,917, which is hereby incorporated by reference, can be used as radically polymerizable binder.

Mixtures of the above-named monomers are preferably used.

Alternatively, cationic monomers can be used as binder, for example cationically ring-opening polymerizable monomers such as glycidyl ethers or cycloaliphatic epoxides, cyclic ketene acetals, spiro orthocarbonates, oxetanes or bicyclic orthoesters. Preferred examples are 2-methylene-1,4,6-tri-oxaspiro[2.2]nonane, 3,9-dimethylene-1,5,7,11-tetraoxa-spiro[5.5]undecane, 2-methylene-1,3-dioxepane, 2-phenyl-4-methylene-1,3-dioxolane, bisphenol A diglycidyl ether, 3,4-epoxycyclohexylmethyl 3,4-epoxycyclohexanecarboxylate, bis(3,4-epoxycyclohexylmethyl) adipate, vinyl cyclohexene dioxide, 3-ethyl-3-hydroxymethyloxetane, 1,10-decanediyl-bis-(oxymethylene)-bis-(3-ethyloxetane) or 3,3-(4-xylylenedioxy)-bis-(methyl-3-ethyloxetane) as well as the epoxides named in EP 0 879 257 B1 and corresponding U.S. Pat. Nos. 6,908,953 and 6,245,828, which US patents are hereby incorporated by reference. Silicic acid polycondensates, which can be obtained for example by hydrolytic condensation of silanes which bear cationically polymerizable groups, preferably epoxide, oxetane or spiro orthoester groups, are also suitable as cationically polymerizable binders. Such silicic acid polycondensates are described, for example, in DE 41 33 494 C2 or U.S. Pat. No. 6,096,903, which is hereby incorporated by reference. Moreover, vinyl ethers, such as e.g. ethyl or isobutyl vinyl ether, as well as N-vinylpyrrolidone, can also be used as cationic monomers.

The volume expansion component (b) has the main purpose of bringing about a transfer of the support or construction material from the carrier substrate onto the receiver substrate. In order that the absorbed energy leads to a controlled droplet formation, the volume expansion component is to be converted into the gas phase in the shortest time due to the heat pulse.

The materials according to the invention are characterized in that they contain at least one reactive, preferably a radically polymerizable, volume expansion component.

Low-boiling liquid monomers and in particular mono (meth)acrylates are preferred as volume expansion component. By low-boiling monomers is meant monomers with a boiling point of less than 200° C. at standard pressure. Methyl (meth)acrylate, ethyl (meth)acrylate, propyl (meth) acrylate, butyl (meth)acrylate, pentyl (meth)acrylate, hexyl (meth)acrylate and N,N-dimethylacrylamide are particularly preferred.

Volume expansion components which have a high vapour pressure, such as e.g. of methyl or ethyl methacrylate, evaporate after deposition on the receiver side and form an oxygen-poor gas layer above the printed construction material. The evaporation of the volume expansion component on the receiver side is advantageous because the inhibiting action of oxygen during the curing of the construction material is hereby reduced or even completely prevented without the use of a protective gas such as e.g. argon, helium, nitrogen or $CO_2$ being necessary.

On the other hand, vapour pressures that are too high can lead to problems on the carrier side, such as the formation of cracks or pores. These problems are caused by an evaporation of the volume expansion component that is too rapid. According to the invention those substances which have a vapour pressure of at most 60 mbar, particularly preferably at most 40 mbar, at 20° C. are preferred as volume expansion component.

The named volume expansion components are characterized in that, unlike unreactive volume expansion components, they participate in the reaction during the curing of the materials and are incorporated into the polymer network. In clinical use, therefore, they are not dissolved out of the material, which is a significant advantage with regard to the production of dental restorations.

In addition, solid, homogeneously dispersed organic substances which decompose abruptly into gases at temperatures of 80°-280° C., for example azobis(isobutyronitrile) (AIBN), can be used as volume expansion component.

The material according to the invention furthermore contains an initiator for the polymerization (c), preferably an initiator for the radical polymerization and quite particularly preferably a photoinitiator for the radical polymerization, for example a photopolymerization initiator for the UV range, a photopolymerization initiator for the visible range or a mixture thereof.

The longest wavelength absorption maximum of the photopolymerization initiator for the UV range preferably lies at a wavelength of less than 400 nm, in particular in the range of from 300 to less than 400 nm, preferably in the range of from 330 to less than 400 nm, particularly preferably in the range of from 345 to less than 400 nm and most preferably in the range of from 360 to less than 400 nm.

The longest wavelength absorption maximum of the photopolymerization initiator for the visible range preferably lies at a wavelength of at least 400 nm, in particular in the range of from 400 to 600 nm, particularly preferably in the range of from 400 to 500 nm and most preferably in the range of from 420 to 480 nm.

The absorption spectra of the photopolymerization initiators can overlap within certain limits. The difference between the longest wavelength absorption maxima of the first and second photopolymerization initiators is preferably at least 5 nm, in particular at least 10 nm, most preferably at least 15 nm. Moreover it is preferred if the first photopolymerization initiator in the wavelength range of from 420 to 750 nm and in particular in the wavelength range of from 440 to 700 nm has a molar decadic absorption coefficient of less than 10 1/(mol·cm).

In particular phosphine oxides, benzoins, benzil ketals, acetophenones, benzophenones, thioxanthones as well as mixtures thereof are suitable as photopolymerization initiators for the UV range. Acyl- and bisacylphosphine oxides such as 2,4,6-trimethylbenzoyldiphenylphosphine oxide or bis-(2,4,6-trimethylbenzoyl)phenylphosphine oxide, benzoin, benzoin alkyl ether, benzil dialkyl ketals such as benzyl dimethyl ketal, α-hydroxyacetophenones such as 1-hydroxy-cyclohexyl-phenyl-ketone, 2-hydroxy-2-methyl-1-phenyl-1-propanone or 2-hydroxy-1-[4-(2-hydroxyethoxy)-phenyl]-2-methyl-1-propanone, α-dialkoxyacetophenones, α-aminoacetophenones such as 2-benzyl-2-(dimethylamino)-1-[4-(4-morpholinyl)-phenyl]-1-butanone or 2-methyl-1-[4-(methylthio)-phenyl]-2-(4-morpholinyl)-1-propanone, alkylthioxanthones such as i-propylthioxanthone as well as mixtures thereof are particularly suitable. Acyl- and bisacylphosphine oxides and in particular 2,4,6-trimethylbenzoyldiphenylphosphine oxide, bis-(2,4,6-trimethylbenzoyl)-phenylphosphine oxide and mixtures thereof are particularly preferred.

In particular α-diketones, acylgermanium compounds, metallocenes as well as mixtures thereof are suitable as photopolymerization initiators for the visible range. α-Diketones such as camphorquinone, 9,10-phenanthrenequinone, 1-phenyl-propane-1,2-dione, diacetyl, 4,4'-dichlorobenzil or derivatives thereof, monoacyl- and diacylgermanium compounds such as benzoyltrimethylgermanium, dibenzoyldiethylgermanium or bis-(4-methoxybenzoyl)-diethylgermanium, titanocenes such as bis-($\eta^5$-2,4-cyclopentadien-1-yl)-bis-[2,6-difluoro-3-(1H-pyrrol-1-yl)phenyl]-titanium as well as mixtures thereof are particularly suitable. α-Diketones and in particular camphorquinone, 1-phenylpropane-1,2-dione and mixtures thereof are particularly preferred. Monoacyltrialkyl- and diacyldialkylgermanium compounds and in particular benzoyltrimethylgermanium, dibenzoyldiethylgermanium, bis-(4-methoxybenzoyl)-diethylgermanium and mixtures thereof are likewise particularly preferred. Mixtures of at least one α-diketone and at least one acylgermanium compound are also quite particularly preferred.

α-Diketones are preferably used in combination with amine accelerators. Tertiary amines are usually used as amine accelerators. In particular tertiary aromatic amines such as N,N-dialkyl-anilines, N,N-dialkyl-p-toluidines or N,N-dialkyl-3,5-xylidines, p-(N,N-dialkylamino)-phenyl ethanols, p-(N,N-dialkylamino)-benzoic acid derivatives, p-(N,N-dialkylamino)-benzaldehydes, p-(N,N-dialkylamino)-phenyl acetic acid esters or p-(N,N-dialkylamino)-phenyl propionic acid esters are suitable. Specific examples of these are N,N-dimethylaniline, N,N-dimethyl-p-toluidine, 3,5,N,N-tetramethylaniline, p-(N,N-dimethylamino)-benzaldehyde, p-(dimethylamino)-benzoic acid ethyl ester and p-(dimethylamino)-benzonitrile as well as mixtures thereof. Tertiary aliphatic amines such as tri-n-butylamine, 2-dimethylaminoethanol, triethanolamine, dimethylaminoethyl methacrylate, N,N-dimethylbenzylamine, heterocyclic amines such as 1,2,2,6,6-pentamethylpiperidine, amino acid derivatives such as N-phenylglycine as well as mixtures thereof are also suitable. p-(Dimethylamino)-benzoic acid ethyl ester, dimethylaminoethyl methacrylate, N,N-dimethylaniline, N,N-dimethyl-p-toluidine, triethanolamine and mixtures thereof are particularly preferred. In particular those photopolymerization initiators which bleach during the introduction of radiation with an emission maximum at a wavelength of at least 400 nm and thus no longer have any disruptive intrinsic colour after the further curing are preferred here. This is true in particular for the named acylgermanium compounds.

In a preferred embodiment a mixture of at least one germanium compound with at least one α-diketone in combination with at least one amine accelerator is used as photopolymerization initiator for the visible range. Quite particularly preferred combinations of these photopolymerization initiators are described in EP 2 649 981 A1 and corresponding U.S. Pat. No. 9,532,930, which is hereby incorporated by reference.

The use of two or more photoinitiators which are active in different wavelength ranges is preferred according to the invention. The first photoinitiator is active in the wavelength range which is used for the curing of the materials in step (3), the second initiator is active in the wavelength range which is used for the post-curing in step (6). Preferred initiator combinations are described e.g. in EP 2 751 618 A2 and corresponding U.S. Pat. No. 9,387,056, which is hereby incorporated by reference.

Reactive construction materials based on cationically polymerizable monomers can preferably be cured with the known cationic photoinitiators, particularly with diaryliodonium or triarylsulphonium salts, optionally in the presence of suitable sensitizers, such as e.g. camphorquinone, monoacyltrialkyl- or diacyldialkylgermanium compounds, such as e.g. benzoyltrimethylgermanium, dibenzoyldiethylgermanium or bis(4-methoxybenzoyl)diethylgermanium. Examples of suitable diaryliodonium salts which can be used with camphorquinone, monoacyltrialkyl- or diacyldialkylgermanium compounds or thioxanthones as sensitizer in the visible range are the commercially available substances 4-octyloxyphenylphenyliodonium hexafluoroantimonate and isopropylphenylmethylphenyliodonium tetrakis(pentafluorophenyl)borate.

The preferably also present energy transformation component (d) is tuned to the wavelength of the laser light to be absorbed. According to the invention inorganic and in particular organic dyes and pigments are preferred as energy transformation component.

In particular dyes and pigments which absorb in the wavelength range of the radiation source used, preferably laser, are preferred. For example, for a neodymium:YAG laser with a wavelength of 1064 nm the following dyes/pigments are particularly preferred: Carbon Black, Sudan Black B (CAS 4197-25-5), Bismarck Brown Y (CAS 10114-58-6), 1-butyl-2-[2-[3-[(1-butyl-6-chlorobenz[cd]indol-2(1H)-ylidene)ethylidene]-2-chloro-1-cyclohexen-1-yl]ethenyl]-6-chlorobenz[cd]indolium tetrafluoroborate (CAS 155613-98-2) or Safranin O (CAS 477-73-6). Carbon Black, Sudan Black B (CAS 4197-25-5) and Safranin O (CAS 477-73-6) are quite particularly preferred.

For a green laser, e.g. with a wavelength of 532 nm, the following dyes/pigments are preferred: Carbon Black, Sudan Red 7B (Oil Violet CAS 6368-72-5), Sudan IV (CAS 85-83-6), Sudan Red G (CAS 1229-55-6), Pigment Red 144 (CAS 5280-78-4), Safranin O (CAS 477-73-6).

For a blue laser, e.g. with a wavelength of 405 nm, the following dyes/pigments are preferred: Carbon Black, Pigment Yellow 93 (CAS 5580-57-4), Sudan Yellow 146 (CAS 4314-14-1), Disperse Yellow 7 (CAS 6300-37-4).

The energy transformation component absorbs the bulk of the energy of the applied energy pulse, for example of the incident laser beam, and converts it into heat. The thus-generated heat pulse is transferred onto the volume expansion component and leads to its abrupt expansion, for example to the abrupt formation of microscopic gas bubbles due to evaporation of the volume expansion component. The transfer of the support or construction material from the carrier substrate onto the receiver substrate is induced hereby. The support or construction material is deposited on the receiver substrate.

The energy transformation component used can, in addition, also be used for the targeted staining of the workpiece.

The construction material according to the invention is preferably designed such that the generated heat pulse locally melts or softens the material or lowers the viscosity in order to guarantee an optimum droplet formation.

The use of an energy transformation eliminates the need for carrier films coated with absorbent coatings made of titanium or other substances, thus avoiding the associated drawbacks.

In addition to the energy transformation component, the materials according to the invention can advantageously contain further chromophoric components. Inorganic and organic pigments are preferred as chromophoric component, particularly heavy-metal-free, i.e. in particular Cd- and Pb-free, pigments. The most common inorganic pigments are those based on the various iron oxides, chromates and molybdates. Azo pigments, such as monoazo, disazo, benzimidazolone and isoindolonone pigments, as well as polycyclic pigments, such as phthalocyanine, thioindigo, flavanthrone, dioxazine and anthanthrone pigments, are mainly used as organic pigments. These substance classes are modified with respect to the colour shade and the colour depth through the use of different substituents. The production, use and properties of the most common organic pigments are described in detail in Herbst/Hunger, "Industrielle Organische Pigmente" [Industrial Organic Pigments], VCH-Verlagsgesellschaft [VCH publishing company], Weinheim, 1987.

Ultramarine blue, pigments based on iron oxide, titanium dioxide, cobalt oxide, aluminium oxide, chromium oxide, nickel oxide, zirconium oxide and/or zinc oxide, carbon black and organic coloured pigments are particularly suitable as pigments. Furthermore, organic pigments, such as for example red diazo condensation pigments, e.g. Microlith® red BR-T (from CIBA, Specialities), and yellow benzimidazolone pigments, e.g. PV Fast Yellow H2G 01 (from Hoechst), are suitable. The iron oxide pigments can have a red, yellow, brown or black colour. Preferred pigments are black iron oxide, brown iron oxide, yellow organic pigment, red organic pigment and titanium dioxide.

The question of whether a chromophoric component serves merely for the colouring or also as energy transformation component depends primarily on the wavelength of the laser light used. Substances which absorb in the wavelength range of the laser are also at least partially effective as energy absorption component.

In addition to the named substances, the construction materials according to the invention can preferably contain further components, in particular one or more fillers, phase change agents, wetting agents, stabilizers and other additives.

Preferred fillers are organic or inorganic filler particles. Preferred inorganic particulate fillers are amorphous spherical materials based on oxides such as $ZrO_2$ and $TiO_2$ or mixed oxides of $SiO_2$, $ZrO_2$ and/or $TiO_2$ with a mean average particle size of from 0.005 to 2 µm, preferably 0.1 to 1 µm, nanoparticulate or microfine fillers such as pyrogenic silica or precipitated silica with a mean average particle size of from 5 to 200 nm, preferably 10 to 100 nm, minifillers such as quartz, glass ceramic or glass powder with an average particle size of from 0.01 to 10 µm, preferably 0.1 to 1 µm, as well as radiopaque fillers such as ytterbium trifluoride or nanoparticulate tantalum(V) oxide or barium sulphate with a mean average particle size of from 10 to 1000 nm, preferably 100 to 300 nm.

Unless otherwise indicated, all particle sizes here are the average value ($d_{50}$ value) of the volume distribution which is measured by dynamic light scattering for particles smaller than 5 micrometres and by static light scattering for particles larger than 5 micrometres. To measure the particle size the particles are suspended in a suitable liquid at a concentration of 0.1 wt.-%. If the particles are resistant to hydrolysis (e.g. $ZrO_2$, $Al_2O_3$, ZTA, ATZ), deionized water is used. The pH is adjusted with an acid or base such that it is at least 2, or better 3 pH units away from the isoelectric point (literature values) of the particles. The samples are treated with ultrasound before and during the measurement. In the case of hydrolysis-sensitive particles (e.g. lithium disilicate), a solvent is used which does not attack the particles, for example tripropylene glycol. In this case, the pH is not adapted. To improve the dispersibility, a suitable surface modifier can be added, for example Solplus™ $^D$540 from Lubrizol.

So-called isofillers are further preferred. These are ground polymers which preferably contain an inorganic filler. Polymers which are obtained by polymerization of the above-defined radically polymerizable binders (binder a) are preferred. The above-named fillers and in particular silanized, highly dispersed silicic acids, glasses and radiopaque fillers such as ytterbium fluoride are preferred as inorganic fillers. Isofillers serve to increase the filler loading, to reduce the polymerization shrinkage and to control the consistency and aesthetics of the processed materials.

According to the invention preferred phase change agents are monomers with wax-like properties for setting the storage viscosity. The phase change agents bring about a phase change from solid (after depositing and cooling on the carrier) to liquid (liquefaction due to heat input by the laser). Preferred phase change agents are stearyl methacrylate, tris(2-hydroxyethylisocyanurate trimethacrylate as well as the wax-like polymerizable substances described in DE 196 26 356 A1.

By the storage viscosity is meant the viscosity which the materials according to the invention have under usual storage conditions, i.e. in particular at room temperature (25° C.). A high viscosity at storage temperature reduces the sedimentation of pigments or fillers.

In order to obtain a homogeneous mixture, the phase change agent is preferably mixed with the remaining components above its melting point. For this, the phase change agent is preferably blended with the main body at room temperature first and then the mixture is heated under continuous stirring. All following steps are carried out at temperatures above the melting point of the phase change agent.

According to the invention preferred wetting agents are surfactants. These serve to set the surface tension and to set the interfacial tension between construction material and carrier, between support material and receiver and between support material and construction material. Through the setting of surface and interfacial tension it is ensured that the layer of the construction material applied to the carrier does not contract (bulging effect), that it forms a homogeneous layer on the receiver and that the construction material does not contract on the support material (bulging effect). Preferred surfactants are conventional ionic (e.g. stearic acid), amphoteric (N,N,N-trimethylammonioacetate) and preferably non-ionic surfactants (polyalkylene glycol ethers (fatty alcohol ethoxylates (FAEO)). In addition to the interface-adapting function, certain surfactants, particularly the above-defined non-ionic surfactants, also have a support function.

Preferred stabilizers are methylhydroquinone (MEHQ) and 2,6-di-tert-butyl-p-cresol (BHT), hydroquinone (HQ) and (2,2,6,6-tetramethylpiperidin-1-yl)oxidanyl (TEMPO). Stabilizers primarily serve to improve the storage stability of the materials.

In addition, the materials used according to the invention can contain further additives, in particular rheology modifiers, such as polyvinyl alcohol, hydroxyethyl cellulose, carboxymethyl cellulose, modified fat derivatives, polyvinylpyrrolidone; fragrances and flavouring agents, such as 2-benzylideneheptanal (amyl cinnamaldehyde), ethyl 2-naphthyl ether and essential oils. Furthermore preservatives with antimicrobial and fungicidal action such as polyformaldehyde, parabens such as 4-hydroxybenzoic acid methyl ester, 4-hydroxybenzoic acid butyl ester or salts thereof, micro- or nanoparticulate silver as well as propionic acid and salts thereof come into consideration as additives. Moreover, the compositions according to the invention can contain solvents such as water or ethanol or corresponding solvent mixtures, fluoride-ion-releasing additives, optical brighteners and/or plasticizers as further additives.

To achieve optimal printing results, it is necessary to match the type and quantities of the components used in the material.

The named constituents are preferably used in the following quantities. All data are in wt.-% and are relative to the total mass of the material.

| Component | preferably | particularly preferably | quite particularly preferably |
|---|---|---|---|
| Binder (a) | 20-98% | 40-95% | 58-90% |
| Chromophoric component | 0-10% | 0.01-5% | 0.1%-2% |
| Energy transformation component (d) | 0-5% | 0.001-2% | 0.05-1% |
| Volume expansion component (b) | 0.5-15% | 1-10% | 1.5-7% |
| Phase change agent | 0-10% | 0-8% | 0-5% |
| Filler | 0-78% | 0-50% | 0-40% |
| Initiator (c) | 0.05-5% | 0.1-3% | 0.2-2% |
| Stabilizer | 0.001%-0.1% | 0.005-0.07% | 0.01-0.05% |
| Wetting agent | 0-2% | 0-1% | 0-0.5% |

According to the invention it has been found that the named substances can be mixed well with each other and homogeneous compositions result. The quantitative proportions of the components can be varied within the named ranges, with the result that the viscosity and the surface tension can be set in a targeted manner.

The construction materials according to the invention preferably have a viscosity of from 0.025 Pas to 1000 Pas and a surface tension of from 20 to 150 mN/m.

Unless otherwise indicated, the viscosity is measured with an Anton Paar rheometer with CP50-1 cone-plate measuring equipment at a shear rate of 100/s and at the processing temperature. In the case of construction materials without phase change agent this is preferably 25° C. and in the case of construction materials with phase change agent preferably lies in the range of 40°-70° C.

The surface and interfacial tension is determined, unless otherwise indicated, according to DIN 55660-1 to -7 or DIN 53914 (Determining the surface tension of surfactants) at 25° C.

The formation of droplets with a defined size without the formation of so-called "satellites" is essential for a reproducible printing process. By satellites is meant smaller droplets which form in addition to the "main droplet" and impair the print quality. The droplet formation is influenced decisively by temperature, airflow and the time between the application of the carrier layer by doctor blade and the droplet generation. The dimensional stability of the printing material layer on the receiver under thermal load and the property change are furthermore important for the accuracy of the printing process.

The materials according to the invention are preferably printed together with a suitable support material. The support materials should preferably behave inertly in combination with the construction materials used. The construction materials are printed together, preferably sequentially, with the support material.

Support materials which in the solidified state contain no components which react with the construction material used are preferred according to the invention. That would make it more difficult to remove the support materials from the shaped body. In general, those support materials which exclusively contain organic components are preferred. After the curing of the workpiece the support material is removed from the shaped body as described above.

Support materials which contain
(α) at least one energy transformation component,
(β) at least one volume expansion component and
(γ) at least one binder are preferred,
wherein non-metallic substances which are solid in pure form at room temperature are preferred as binder. The binder primarily carries out the support function.

The energy transformation component (α) in the support material is tuned to the wavelength of the laser light to be absorbed. According to the invention inorganic and in particular organic dyes and pigments are preferred as energy transformation component. In particular dyes and pigments which absorb in the wavelength range of the radiation source used, preferably laser, are preferred. For example, for a neodymium:YAG laser with a wavelength of 1064 nm the following dyes/pigments are particularly preferred: Carbon Black, Sudan Black B (CAS 4197-25-5), Bismarck Brown Y (CAS 10114-58-6), 1-butyl-2-[2-[3-[(1-butyl-6-chlorobenz [cd]indol-2(1H)-ylidene)ethylidene]-2-chloro-1-cyclo-hexen-1-yl]ethenyl]-6-chlorobenz[cd]indolium tetrafluoroborate (CAS 155613-98-2) or Safranin O (CAS 477-73-6).

For a green laser, e.g. with a wavelength of 532 nm, the following dyes/pigments are preferred: Carbon Black, Sudan Red 7B (Oil Violet CAS 6368-72-5), Sudan IV (CAS 85-83-6), Sudan Red G (CAS 1229-55-6), Pigment Red 144 (CAS 5280-78-4), Safranin O (CAS 477-73-6).

For a blue laser, e.g. with a wavelength of 405 nm, the following dyes/pigments are preferred: Carbon Black, Pigment Yellow 93 (CAS 5580-57-4), Sudan Yellow 146 (CAS 4314-14-1), Disperse Yellow 7 (CAS 6300-37-4).

The volume expansion component (β) has the main purpose of bringing about a transfer of the printing material from the carrier onto the receiver substrate. In order that the absorbed energy leads to a controlled droplet formation, the volume expansion component is to be converted into the gas phase in the shortest time due to the heat pulse. A substance with a boiling point of 80-280° C. and particularly preferably of 95-200° C. is preferably used as volume expansion component (boiling points at standard pressure). Preferred substances are 1,8-octanediol and 1,6-hexanediol. Substances which are liquid at 25° C., in particular water and 1-octanol, are particularly preferred. Water has the advantage that no solvent vapours which are hazardous to health or potentially explosive form during the evaporation.

Further preferred substances which can be used as volume expansion component (β) are propylene glycol diacetate, ethylene glycol diacetate, triethyl-2-acetyl citrate, triethyl citrate, adipic acid dimethyl ester, adipic acid diethyl ester, triethylene glycol, glutaric acid diethyl ester, glutaric acid dimethyl ester, diethyl succinate, acetic acid butyl ester, acetic acid n-hexyl ester. The volume expansion component is preferably matched to the binder used such that the viscosity, the surface tension and the homogeneity lie within the ranges defined herein. A homogeneity suitable according to the invention exists when there is no visible phase separation. For this, polar binders such as PEG, PVA are preferably combined with a polar volume expansion component such as e.g. water, and non-polar binders such as paraffin are preferably combined with a less polar volume expansion component such as 1-octanol.

Alternatively, solid, homogeneously dispersed organic substances which decompose abruptly into gases at temperatures of 80°-280° C., for example azobis(isobutyronitrile) (AIBN), can be used as volume expansion component (β).

Polymers, waxes and/or non-ionic surfactants which are solid at a temperature below 40° C. are preferably used as binder (γ).

Polymers preferred according to the invention are glycol polymers, in particular polyethylene glycol (PEG), polypropylene glycol (PPG), PEG-PPG copolymers and PVA. Polyethylene glycol (PEG) with a molecular weight of 1500-10,000 g/mol is particularly preferred. Crosslinked polymers such as polyacrylamide, polyvinylpyrrolidone, amylopectin, gelatin, cellulose, polymers based on polyacrylic acid and in particular copolymers of acrylic acid or sodium acrylate with acrylamide are further preferred. These crosslinked polymers are polar and can form hydrogels. Polar polymers are particularly suitable for combination with a polar volume expansion component such as water.

The term "wax" is to be understood as defined by the Deutsche Gesellschaft für Fettwissenschaft [German for Fat Science] in DGF standard method MI1 (75). As the chemical composition and origin of different waxes vary greatly, waxes are defined via their mechanical-physical properties. A substance is called a wax if it is kneadable, solid to brittle hard, has a coarse to fine-crystalline structure, is translucent to opaque in terms of colour but is not glassy at 20° C.; above 40° C. it melts without decomposition, is readily liquid even slightly above the melting point (low-viscosity) and not stringy; has a strongly temperature-dependent consistency and solubility, and can be polished under slight pressure. Waxes typically change into the molten state between 40° C. and 130° C.; as a rule waxes are insoluble in water. Waxes for use in the support material according to the invention preferably have a melting point in the range of from 40 to less than 80° C., particularly preferably of from 45 to 65° C.

Waxes are divided into three main groups depending on their origin, namely natural waxes, wherein here a distinction is in turn made between plant and animal waxes, mineral waxes and petrochemical waxes; chemically modified waxes and synthetic waxes. The wax used as binder in the support material according to the invention can consist of one wax type or also of mixtures of different wax types.

Petrochemical waxes, such as for instance paraffin wax (hard paraffin), petrolatum, microcrystalline wax (micro paraffin) and mixtures thereof, are preferred; paraffin wax is particularly preferred. Paraffin waxes which are commercially available as injection-moulding binders for manufacturing oxide-ceramic and non-oxide-ceramic components in the hot-casting process (low-pressure injection moulding) are very suitable, e.g. paraffin wax with a melting point of approx. 54-56° C., a viscosity of 3-4 mPa·s at 80° C. Commercially available waxes often already contain emulsifiers and/or further components for adapting the rheology.

Plant waxes, e.g. candelilla wax, carnauba wax, Japan wax, esparto wax, cork wax, guaruma wax, rice bran wax, sugarcane wax, ouricury wax, montan wax; animal waxes, e.g. beeswax, shellac wax, spermaceti, lanolin (wool wax), rump fat; mineral waxes, e.g. ceresin, ozokerite (earthwax); chemically modified waxes, e.g. montan ester waxes, sasol waxes, hydrogenated jojoba waxes, or synthetic waxes, e.g. polyalkylene waxes, polyethylene glycol waxes, can also be used as wax.

Non-ionic surfactants are substances with interface-active properties which do not form ions in aqueous media. These are molecules which have a hydrophobic portion and a hydrophilic portion. The overall hydrophobicity of the molecules can be set through the choice of the length and type of the hydrophobic and hydrophilic portions.

Support materials which contain a surfactant with a melting point of from 40° C. to 120° C., preferably 45° C. to 80° C., as non-ionic surfactant (γ) are preferred.

Preferred non-ionic surfactants are the ethoxylates of fatty alcohols, oxo alcohols or fatty acids, fatty acid esters of sugars and hydrogenated sugars, alkyl glycosides as well as block polymers of ethylene and propylene oxide, in particular short-chain block co-oligomers.

Fatty acid esters of hydrogenated sugars are particularly preferred, in particular those with the formula R'-CO-O-sugar, wherein R' is a branched or preferably straight-chain alkyl radical with 10 to 25 carbon atoms, preferably 12 to 22 carbon atoms. Straight-chain alkyl radicals with 15 to 22 carbon atoms are preferred. "Sugar" stands for a hydrogenated sugar radical which is preferably ethoxylated 0 to 5 times. Fatty acid esters of sorbitol are quite particularly preferred, in particular sorbitan stearates such as e.g. sorbitan monostearate (CAS 1338-41-6).

A further preferred group of surfactants are ethoxylates of fatty acids, in particular those with the general formula R''-(CO)-(OCH$_2$CH$_2$)m-OH, in which R'' is a branched or preferably straight-chain alkyl radical with 10 to 25 carbon atoms, preferably 12 to 22 carbon atoms. Straight-chain alkyl radicals with 16 to 22 carbon atoms are particularly preferred. m is an integer from 0 to 20, preferably 0 to 10 and particularly preferably 0 to 6.

Quite particularly preferred surfactants (γ) are fatty alcohols and ethoxylates of fatty alcohols, in particular polyalkylene glycol ethers with the general formula R-(OCH$_2$CH$_2$)n-OH, in which R is an alkyl radical with 10 to 20 carbon atoms and n is an integer from 0 to 25. R can be a branched or preferably straight-chain alkyl radical, wherein alkyl radicals with 12 to 25 carbon atoms and particularly straight-chain alkyl radicals with 12 to 22 carbon atoms are preferred. Quite particularly preferred alkyl radicals are lauryl, cetyl, cetearyl and stearyl.The polyalkylene glycol ethers can be obtained by reacting the corresponding fatty alcohols with ethylene oxide (EO). The index n indicates the number of ethylene oxide radicals. Polyalkylene glycol ethers with 0 to 21 (n=2-21), in particular 0 to 12 (n=2-12) and quite particularly 0 to 5 (n=2-5) ethylene oxide radicals are preferred. Examples of polyalkylene glycol ethers preferred according to the invention are compounds in which R is a cetyl radical ($C_{16}$ radical) and n is 20 and in particular 2. These compounds have the INCI names Ceteth-2 and Ceteth-20. Ceteth-2 has e.g. the formula $C_{16}H_{33}$—$(OCH_2CH_2)_2$—OH. Compounds in which R is a stearyl radical ($C_{18}$ radical) and n is 2, 10, 20 or 21 are further preferred. These compounds have the INCI names Steareth-2, Steareth-10, Steareth-20 and Steareth-21. Steareth-2 has e.g. the formula $C_{18}H_{37}$—$(OCH_2CH_2)_2$—OH. Quite particularly preferred non-ionic surfactants are Steareth-20, Steareth-10, Ceteth-20 and in particular Steareth-2 and Ceteth-2. Mixtures of different non-ionic surfactants and in particular different polyalkylene glycol ethers can likewise be used.

Binders (γ) with a melting point between 40° C. and 200° C., particularly preferably 50° C. to 80° C., are preferred, wherein those binders which do not decompose thermally during melting are particularly preferred. In the melted state the binder preferably has a viscosity of below 100 Pas, particularly preferably below 20 Pas and quite particularly preferably below 5 Pas, so that it can be easily removed from the component. The binder should be combustible as residue-free as possible. It is important that the support material in the solid state has a sufficient strength to be able to support the printing material correspondingly.

The support materials preferred according to the invention can additionally contain one or more further surfactants to set the surface tension and to set the interfacial tension between support material and carrier, between support material and receiver and between support material and construction material. Through the setting of surface and interfacial tension it is ensured that the layer of the support material applied to the carrier does not contract (bulging effect), that it forms a homogeneous layer on the receiver and that the construction material does not contract on the support material (bulging effect). Preferred surfactants for setting the surface tension and interfacial tension are ionic surfactants (e.g. stearic acid), amphoteric surfactants (e.g. N,N,N-trimethylammonioacetate) and preferably the above-named non-ionic surfactants, wherein fatty alcohol ethoxylates (FAEO) and polyalkylene glycol ethers are particularly preferred here. In addition to the interface-adapting function, certain surfactants, particularly the above-defined non-ionic surfactants, also have a support function.

The support materials preferred according to the invention preferably have a viscosity of from 0.2 Pas to 1000 Pas and a surface tension of from 20 to 150 mN/m, preferably 30 to 100 mN/m and particularly preferably 40 to 90 mN/m.

In addition to the named substances, the support materials preferred according to the invention can preferably contain one or more additives. Preferred additives are stabilizers such as methylhydroquinone (MEHQ) and 2,6-di-tert-butyl-p-cresol (BHT); rheology modifiers such as polyvinyl alcohol, hydroxyethyl cellulose, carboxymethyl cellulose, polyvinylpyrrolidone; fragrances, such as 2-benzylideneheptanal (amyl cinnamaldehyde), ethyl 2-naphthyl ether and essential oils; and fillers. Organic fillers which combust residue-free are preferred. Furthermore, antimicrobial substances such as polyformaldehyde, parabens such as hydroxybenzoic acid methyl ester come into consideration as additives.

The support materials preferred according to the invention preferably contain:

0.05 to 30 wt.-%, particularly preferably 0.05 to 20 wt.-%, energy transformation component (α), 5 to 60 wt.-%, particularly preferably 8 to 50 wt.-%, volume expansion component (β), 35 to 94.95 wt.-%, particularly preferably 40 to 90 wt.-% and quite particularly preferably 49 to 90 wt.-%, binder (γ)

Unless otherwise indicated, all quantities are relative to the total mass of the support material.

The process according to the invention is suitable for the production of shaped bodies made of filled and unfilled plastics.

An advantage of the LIFT process according to the invention is that a wide variety of materials can be deposited selectively and after the material has been applied, can independently cure or solidify according to their properties or can be cured or solidified by an additional process step. Materials with high viscosity and high filler contents can be processed using the process, with the result that components with excellent physical properties, i.e. with high toughness, high breaking strength, good abrasion resistance and a high elastic modulus can be produced. Moreover, it would be possible to use fillers with larger particle sizes than are possible in inkjet processes. The process can be used to produce individual areas of the component in a targeted manner with materials of different composition, for example differently stained materials, with the result that dental restorations with a very natural appearance can be produced.

The invention is explained in more detail below with reference to examples.

EXAMPLES

Examples 1 to 3: Production of Construction Materials

The materials specified in the following Table 1 were produced by mixing the components. The material from Example 1 is particularly suitable for the production of removable partial and total prostheses (prosthesis base material), the material from Example 2 is particularly suitable for the production of occlusal splints for orthodontics (orthodontic material) and the material from Example 3 is particularly suitable for the production of artificial teeth for removable prosthodontics (tooth material).

To produce the materials, binder, stabilizer and optionally wetting agent were homogeneously mixed using a paddle mixer and stirred until the stabilizer had completely dissolved. The mixtures were partly heated to at most 70° C. to reduce the viscosity. Then a small part of this mixture was blended with colour pigments and the energy transformation component. The pigments were solubilized in a three-roll mill and dispersed until a homogeneously stained mixture was obtained. This mixture was then added to the bulk of the starting mixture and stirred until a homogeneous mixture had formed.

Fillers were optionally stirred into the mixtures by hand and then homogenized using a three-roll mill or a planetary mixer.

The photoinitiators were completely dissolved in the volume expansion component with exclusion of short-wavelength light (<550 nm), this mixture was then added to the prepared bulk and homogeneously mixed using a mixer, a three-roll mill or a planetary mixer. It was possible to process the mixtures using the LIFT process.

TABLE 1

Dental materials according to the invention

| Component | Ex. 1 | Ex. 2 | Ex. 3 |
|---|---|---|---|
| Binder (a) | | | |
| Bis-GMA[1] | 39.5 | 35.0 | 15.0 |
| UDMA[2] | 30.0 | 32.0 | 12.0 |
| EGDMA[3] | 25.0 | — | 9.0 |
| D3MA[4] | — | 22.0 | — |
| Chromophoric component | | | |
| PV Fast Red HF4 B[15] | 0.3 | — | — |
| Microlith Yellow 3G-K[5] | — | — | 0.18 |
| Reactive volume expansion component (b) | | | |
| Butyl methacrylate[6] | 4.0 | 10.0 | 4.0 |
| Filler | | | |
| Pyrogenic silica[7] | — | — | 15.0 |
| Ytterbium fluoride[8] | — | — | 14.0 |
| Isofiller[9] | — | — | 30.0 |
| Energy transformation component (d) | | | |
| Copper phthalocyanine[10] | 0.1 | 0.1 | — |
| Photoinitiator (c) | | | |
| Camphorquinone DL[11] | 0.3 | 0.2 | 0.12 |
| Ethyl 4(dimethylamino)benzoate[12] | 0.5 | 0.4 | 0.20 |
| UV stabilizer | | | |
| 2-(2'-Hydroxy-5'-methylphenyl)benzotriazole[13] | 0.3 | 0.3 | 0.10 |
| Wetting agent | | | |
| Phosphoric acid polyester[14] | — | — | 0.40 |

[1] 2,2-Bis[4-(2-hydroxy-3-methacryloxypropoxy)phenyl]propane (CAS 1565-94-2)
[2] 1,6-Bis[2-methacryloyloxyethoxycarbonylamino]-2,4,4-trimethyl-hexane (CAS 72869-86-4)
[3] Ethylene glycol dimethacrylate (CAS 97-90-5)
[4] 1,10-Decanediol dimethacrylate (CAS 6701-13-9)
[5] CAS 5580-57-4
[6] CAS 97-88-1
[7] Aerosil OX50 (CAS 7631-86-9n)
[8] CAS 13760-80-0
[9] Splinter polymer (microfiller composite ground to powder)
[10] Heliogen Blue L7072D (CAS 147-14-8)
[11] CAS 10373-78-1
[12] Quantacure EPD (CAS 10287-53-3)
[13] Chisorb P (CAS2440-22-4)
[14] Phosphoric acid polyester (72243-070628, Germany)
[15] CAS 59487-23-9

Example 4: Production of Components by LIFT Process

The materials from Examples 1 to 3 and the support material were applied to a plasma-treated 50-μm-thick PET film separately using a doctor blade. The material film thickness was on average 30 μm in all cases.

The carrier substrates were transferred into the working area of the laser and processed there within a maximum of 5 seconds after the application by doctor blade. A neodymium:YAG laser with a wavelength of 1064 nm was used as laser. The coated carriers were fired at from behind through the carrier substrate with a laser pulse of 100 ns with a power of 12 mW, wherein the laser beam was focused on a spot with a diameter of 50 μm.

Plasma-treated PET films with a thickness of 50 μm were used as receiver substrate. The droplets were deposited on the receiver substrate next to each other with an overlap of 0-30 μm, while the material film was continuously renewed on the carrier. The distance between carrier substrate (site of droplet generation, i.e. the point at which the laser fires the droplets from the material layer) and receiver substrate was 300 μm.

On the receiver substrate, the materials 1 to 3 were cured under a constant gas flow of dry nitrogen by means of an LED blue light source for 10 seconds at 460 nm with a power density of 50 mW/cm2.

The support material was deposited on the receiver substrate at selected locations. In the free spaces not printed with support material, the construction material was applied in the described manner. The solidification of the support material was effected by drying, by passing a constant airflow over the receiver substrate for 10 seconds. The support material was dried thereby to the extent that it solidified. In each case 5 layers of support material and 5 layers of construction material were deposited, then the component was smoothed to match the layer height with a tungsten carbide burr with material suction. After the smoothing, further layers were applied and smoothed again.

The procedure was repeated until the printing of the object was finished.

The support material used had the following composition:

| Component | Proportion |
|---|---|
| Deionized water | 49.80 wt.-% |
| Polyethylene glycol 2000 g/mol | 50 wt.-% |
| Safranin O (CAS 477-73-6) | 0.20 wt.-% |

After printing the support and construction materials, the components were removed from the construction chamber, the support material was removed mechanically using a soft toothbrush and lukewarm water and the workpieces were then post-exposed in a Lumamat (Ivoclar Vivadent AG) using programme 2 for 11 minutes and thereby completely cured.

Then the surfaces of the components were polished using a dental polisher (handpiece) with polishing wheel and polishing paste.

The invention claimed is:

1. A construction material for energy-pulse-induced transfer printing (LIFT) comprising,
   (a) at least one polymerizable binder,
   (b) at least one volume expansion component, and
   (c) at least one initiator for the polymerization, and
   further comprising at least one of a chromophoric component, an inorganic pigment comprising iron oxide, chromate or molybdate, and/or at least one organic pigment comprising azo pigments comprising monoazo, disazo, benzimidazolone, isoindolonone pigments, polycyclic pigments comprising phthalocyanine, thioindigo, flavanthrone, dioxazine and anthanthrone pigments.

2. The material according to claim 1, further comprising (d) at least one energy transformation component.

3. The material according to claim 1, wherein the at least one initiator (c) comprises a photoinitiator.

4. The material according to claim 1, wherein the at least one polymerizable binder (a) comprises a radically polymerizable binder, at least one mono- or multifunctional (meth)acrylate or a mixture thereof.

5. The material according to claim 1, wherein the at least one volume expansion component (b) comprises at least one of a reactive polymerizable monomer, a radically polymerizable monomer, one or more mono(meth)acrylates, a methyl (meth)acrylate, an ethyl (meth)acrylate, a propyl (meth)acrylate, a butyl (meth) acrylate, a pentyl (meth) acrylate, a hexyl (meth)acrylate and/or a N,N-dimethylacrylamide.

6. The material according to claim 3,
wherein the photoinitiator comprises an initiator for the UV range comprising at least one of phosphine oxide, benzoin, benzil ketal, acetophenone, benzophenone, thioxanthone or a mixture thereof, an acyl- and bisacylphosphine oxide such as 2,4,6-trimethylbenzoyldiphenylphosphine oxide or bis-(2,4,6-trimethylbenzoyl)phenylphosphine oxide, benzoin, a benzoin alkyl ether, a benzil dialkyl ketal such as benzyl dimethyl ketal, an a-hydroxyacetophenone, 1-hydroxy-cyclohexyl-phenyl-ketone, 2-hydroxy-2-methyl-l-phenyl-1-propanone or 2-hydroxy-1-[4-(2-hydroxyethoxy)-phenyl]-2-methyl-l-propanone, an a-dialkoxyacetophenone, an α-aminoacetophenone, 2-benzyl-2-(dimethylamino)-1-[4-(4-morpholinyl)-phenyl]-1-butanone or 2-methyl-1-[4-(methylthio)-phenyl]-2-(4-morpholinyl) -1-propanone, an alkylthioxanthone, i-propylthioxanthone or a mixture thereof, an acyl- and bisacylphosphine oxide, 2,4,6-trimethylbenzoyldiphenylphosphine oxide, bis-(2,4,6-trimethylbenzoyl)-phenylphosphine oxide or a mixture thereof, and/or a photoinitiator for the visible range comprising at least one of an α-diketone, an acylgermanium compound, a metallocene or a mixture thereof, an α-diketone, camphorquinone, 9,10-phenanthrenequinone, 1-phenyl-propane-1,2-dione, diacetyl, 4,4'-dichlorobenzil or a derivative thereof, a monoacyl- and diacylgermanium compound, benzoyltrimethylgermanium, dibenzoyldiethylgermanium or bis-(4-methoxybenzoyl)-diethylgermanium, a titanocene, bis-($\eta^5$-2,4-cyclopentadien-1-yl)-bis-[2,6-difluoro-3-(1H-pyrrol-1 -yl)phenyl]-titanium or a mixture thereof, an α-diketone, camphorquinone, 1-phenylpropane-1,2-dione or a mixture thereof, a monoacyltrialkyl- or diacyldialkylgermanium compound, benzoyltrimethylgermanium, dibenzoyldiethylgermanium, bis-(4-methoxybenzoyl) -diethylgermanium or a mixture thereof, or a mixture of at least one a-diketone and at least one acylgermanium compound.

7. The material according to claim 2,
wherein the energy transformation component (d) comprises at least one inorganic or organic dye and/or at least one inorganic or organic pigment.

8. The material according to claim 1, further comprising at least one filler, a phase change agent, a wetting agent and/or a stabilizer.

9. The material according to claim 1, comprising
20 to 98 wt.-% binder (a),
0.5 to 15 wt.-% volume expansion component (b) and
0.05 to 5 wt.-% initiator (c), in each case relative to the total mass of the material.

10. The material according to claim 1, comprising
40 to 95 wt.-% binder (a),
1 to 10 wt.-% volume expansion component (b) and
0.1 to 3 wt.-% initiator (c), in each case relative to the total mass of the material.

11. The material according to claim 1, comprising
58 to 90 wt.-% binder (a),
1.5 to 7 wt.-% volume expansion component (b) and
0.2 to 2 wt.-%, initiator (c), in each case relative to the total mass of the material.

12. The material according to claim 9, further comprising
0 to 5 wt.-% energy transformation component and/or
0 to 10 wt.-% phase change agent and/or
0 to 78 wt.-% filler and/or
0.001 to 0.1 wt.-% stabilizer and/or
0 to 2 wt.-% wetting agent, in each case relative to the total mass of the material.

13. The material according to claim 9, further comprising
0.001 to 2 wt.-% energy transformation component and/or
0 to 8 wt.-% phase change agent and/or
0 to 50 wt.-% filler and/or
0.005 to 0.07 wt.-% stabilizer and/or
0 to 1 wt.-% wetting agent, in each case relative to the total mass of the material.

14. The material according to claim 9, further comprising
0.05 to 1 wt.-% energy transformation component and/or
0 to 5 wt.-% phase change agent and/or
0 to 40 wt.-% filler and/or
0.01 to 0.05 wt.-% stabilizer and/or
0 to 0.5 wt.-% wetting agent, in each case relative to the total mass of the material.

15. A system for application of a material by energy-pulse-induced transfer printing, which comprises a material according to claim 1 and a carrier for the material.

16. A process of using the construction material according to claim 1 comprising
producing three-dimensional objects by energy-pulse-induced transfer printing (LIFT).

17. A process for the additive manufacture of three-dimensional objects, which comprises the following steps:
(1) laminar application of a support/construction material to a carrier in a defined layer thickness,
(2) transfer of a portion of the support/construction material from the carrier substrate (donor) onto a receiver substrate (acceptor) by local, site-selection input of an energy pulse,
(3) solidification of the support/construction material on the receiver substrate,
(4) repetition of steps (1)-(3) until the desired object has been constructed,
(5) optionally removal of the support material and optional cleaning of the object,
(6) optional post-curing of the component by further curing,
(7) optional mechanical processing of the object,
characterized in that the material according to claim 1 is used as the construction material.

18. The process according to claim 17 wherein:
(1) the defined layer thickness is 3-300 μm or 10-100 μm,
(2) the local, site-selection input of an energy pulse comprises a laser pulse,
(3) solidification comprises by drying, radiation curing or altering the aggregation state,
(6) further curing comprises by drying, radiation, heat or a combination thereof,
(7) optional mechanical processing of the object comprises vibratory finishing or manual processing comprising grinding or polishing.

19. The process according to claim 17,
in which the support/construction material is smoothed following step (3) by a roller, blade, burr and/or a wiper.

20. The process according to claim 17,
in which in step (2) one or more layers of support material are applied to the receiver substrate and then a construction material is deposited/applied onto or into the previously deposited layers of the support material by means of LIFT.

21. The process according to claim 17,
in which a polymer film, a glass carrier, a carrier made of a non-metallic, inorganic, non-porous material, a metallic carrier or a ceramic carrier is used as carrier in step (1) and/or receiver substrate in step (2).

22. The process according to claim 17,
in which in step (2) a non-porous receiver substrate is used.

23. The process according to claim 17,
in which the energy input in step (2) is effected via a side of the carrier substrate facing away from the support or construction material.

\* \* \* \* \*